US00PP35722P2

(12) United States Plant Patent
Read

(10) Patent No.: US PP35,722 P2
(45) Date of Patent: Apr. 2, 2024

(54) ***GAILLARDIA* PLANT NAMED 'ORANGE RUFFLES'**

(50) Latin Name: ***Gaillardia* x *grandiflora***
Varietal Denomination: Orange Ruffles

(71) Applicant: Charles Richard Read, Bognor Regis (GB)

(72) Inventor: Charles Richard Read, Bognor Regis (GB)

( * ) Notice: Subject to any disclaimer, the term of this patent is extended or adjusted under 35 U.S.C. 154(b) by 0 days.

(21) Appl. No.: 18/114,821

(22) Filed: Feb. 27, 2023

(51) Int. Cl.
*A01H 5/02* (2018.01)
*A01H 6/14* (2018.01)

(52) U.S. Cl.
USPC ..... Plt./431

(58) Field of Classification Search
USPC ..... Plt./431, 226, 263.1
CPC ..... A01H 5/02; A01H 5/00; A01H 6/14
See application file for complete search history.

(56) References Cited

PUBLICATIONS

Grassi. 10 Cast 2022 first day personal favorites, Greenhouse Management retrieved on Jun. 13, 2023 at https://www.greenhousemag.com/news/cast-22-varieties-new-favorite/, 16 pp. (Year: 2022).*

* cited by examiner

*Primary Examiner* — June Hwu
(74) *Attorney, Agent, or Firm* — Weatherly IP Solutions, LLC; James M. Weatherly

(57) ABSTRACT

A new cultivar of *Gaillardia* named 'Orange Ruffles' that is distinguishable by its compact, low-growing and naturally branching plant habit. The newly opened inflorescence of 'Orange Ruffles' bears red ray florets only to be followed by whorls of orange to red inner ray florets as the inflorescence matures. The disc florets of 'Orange Ruffles' bear yellow petals and dark red petal apices. The disc appears dark red when the inflorescence is mature. 'Orange Ruffles' is hardy to USDA Zone 5.

2 Drawing Sheets

Genus and species: *Gaillardia* x *grandiflora*.
Variety denomination: 'Orange Ruffles'.

BACKGROUND

The present invention relates to a new and distinct cultivar of *Gaillardia* plant, also known as a blanket flower, a herbaceous perennial that is grown for use as an ornamental landscape and container plant. The new variety is known botanically as *Gaillardia* x *grandiflora* and will be referred to hereinafter by the variety name 'Orange Ruffles'. *Gaillardia* is in the family Compositae, under which the commonly referred to "flower" is actually the inflorescence, and made up of smaller ray florets and disc florets. The ray florets themselves have the appearance of petals.

'Orange Ruffles' is product of a *Gaillardia* breeding program started in 2012. The breeding program was conducted in a greenhouse in a nursery environment in West Sussex, United Kingdom. The aims of the breeding program were to produce novel combinations of flower colors and flower forms which are borne on well-branched plants with sturdy growth habits. 'Orange Ruffles' was selected in 2018 for its combination of bright red outer ray florets and lighter red inner ray florets, and accented by yellow tips. The combination of outer and inner ray florets confers a ruffled appearance to the inflorescence. 'Orange Ruffles' was also selected for its compact and low-growing plant habit.

'Orange Ruffles' resulted from the controlled pollination of *Gaillardia* seedling code G1317-5 as female parent by *Gaillardia* seedling code G1409-3 as male parent. Both parents had been raised within the inventor's breeding program and are unnamed beyond the code listed above, unreleased and unpatented. The inventor first asexually reproduced 'Orange Ruffles' in 2018 in an unheated greenhouse at the inventor's nursery in West Sussex, United Kingdom using vegetative cuttings. Subsequent asexual propagations have been carried in the same greenhouse using both vegetative cuttings and root cuttings. 'Orange Ruffles' is stable and reproduces true to type in successive generations of asexual reproduction by either method of asexual propagation.

SUMMARY

The following traits have been repeatedly observed and represent the distinguishing characteristics of 'Orange Ruffles'. 'Orange Ruffles' has not been tested under all possible conditions and phenotypic differences may be observed with variations in environmental, climatic, and cultural conditions, without however, any variance in genotype.

1. 'Orange Ruffles' exhibits a compact, low-growing and naturally branching plant habit.
2. A mature plant of 'Orange Ruffles' growing in a 3.7 gallon container is 15 cm to 20 cm in height and 40 cm to 45 cm in diameter.
3. A mature plant of 'Orange Ruffles' growing in a 3.7 gallon container bears approximately 70 flowers and buds at any one time during its main flowering period, March to October.
4. The inflorescences of 'Orange Ruffles' are composed of 55 to 65 ray florets and 125 to 150 disc florets.

5. A newly opened inflorescence of 'Orange Ruffles' bears outer ray florets only. Whorls of inner ray florets develop as the inflorescence matures and ages.
6. The initial (outer) ray florets of 'Orange Ruffles' are predominantly red in color, with small yellow tips. As the inflorescence ages, the outer ray florets fade to lighter red with larger yellow tips which exhibit parallel red veins. The inner ray florets of 'Orange Ruffles' are predominantly orange to red in color.
7. The disc florets of 'Orange Ruffles' bear yellow petals and dark red petal apices. The disc appears dark red when the inflorescence is mature.
8. 'Orange Ruffles' is hardy to USDA Zone 5.

DESCRIPTION OF THE PHOTOGRAPHS

The accompanying color photographs illustrate the overall appearance of the new *Gaillardia* cultivar 'Orange Ruffles' showing the colors as true as it is reasonably possible to obtain in colored reproductions of this type. Colors in the photographs may differ from the color values cited in the detailed botanical description, which more accurately describes the actual colors of the new variety 'Orange Ruffles'. The illustrated plant has been grown without the use of any chemical growth regulators.

DESCRIPTION OF THE NEW VARIETY

Figure 1:
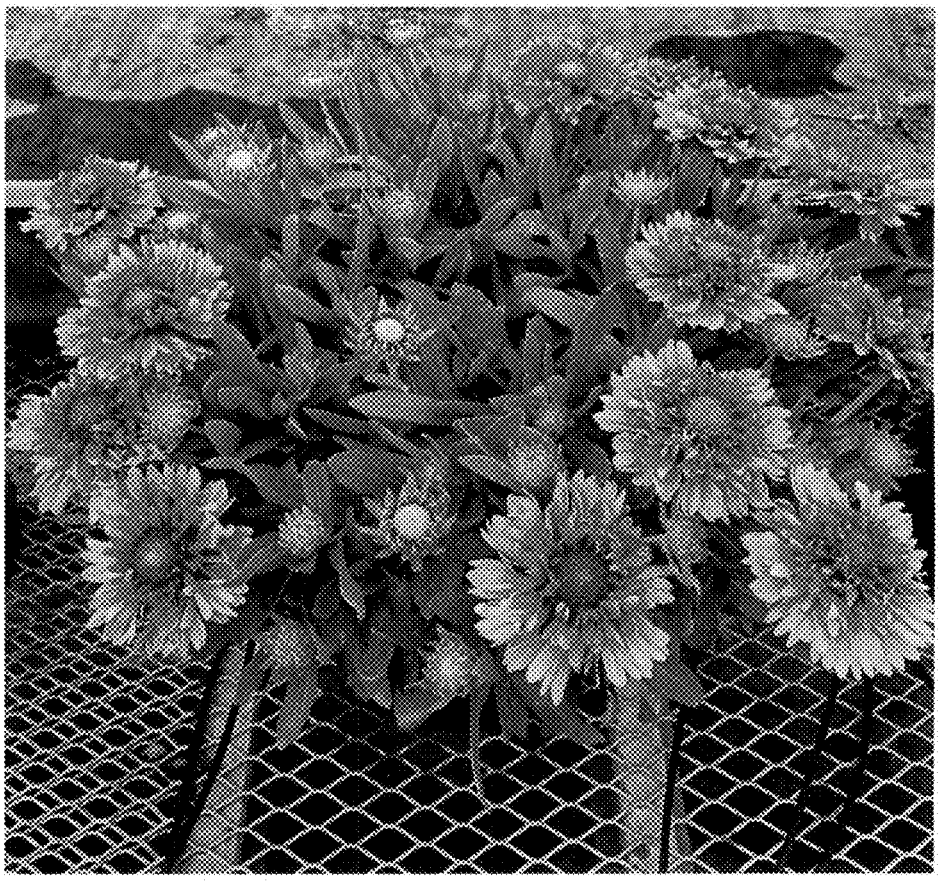
FIG. 1 depicts a whole plant in bud and flower of 'Orange Ruffles' which has been grown in a 3.7 gallon container out of doors in Santa Barbara, California.
Figure 2:
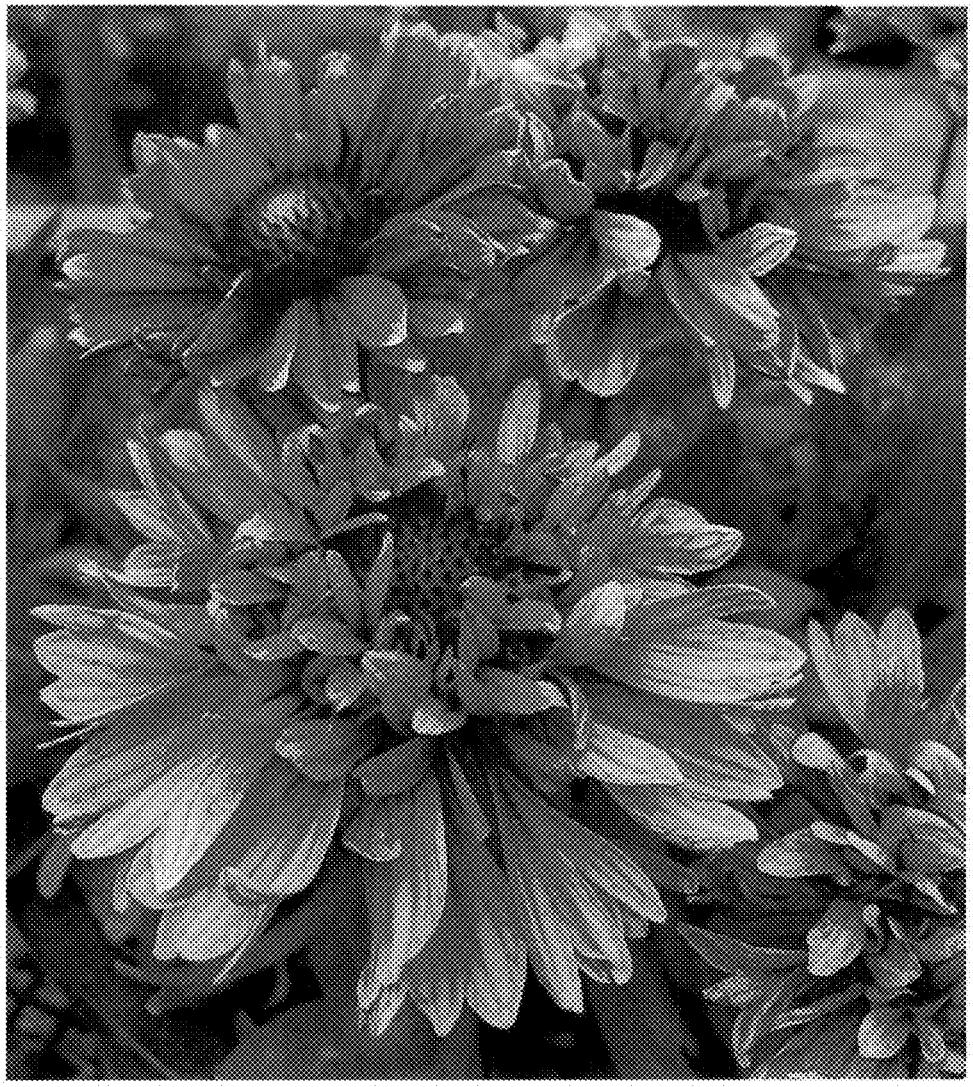
FIG. 2 depicts a close-up view of the young and mature inflorescence of 'Orange Ruffles'.

The following detailed descriptions set forth the distinctive characteristics of 'Orange Ruffles'. Observations, measurements, values, and comparisons were collected in March 2022 in Santa Barbara, California from a fifteen month old plant grown outdoors in full sun in a 3.7 gallon (14 liter) container. Color determinations were made in accordance with The 2007 Royal Horticultural Society Colour Chart from London England, except where general color terms of ordinary dictionary significance are used.

Classification:
- *Family*.—Compositae.
- *Genus*.—*Gaillardia*.
- *Species*.—*X grandiflora*.
- *Common name*.—Blanket flower.

Parentage:
- *Female parent*.—*Gaillardia* code number 'G1317-5' (unreleased, unpatented).
- *Male parent*.—*Gaillardia* code number 'G1409-3' (unreleased, unpatented).

Plant:
- *Propagation method*.—Typically by softwood cuttings although root cuttings have also been successful.
- *Root system*.—Fine and fibrous.
- *Vigor*.—Moderate vigor.
- *Time to initiate roots*.—Approximately 14 to 20 days are needed to develop roots on initial cuttings.
- *Temperatures to initiate rooting*.—The recommended air temperature is 20° C.-21° C.
- *Crop time*.—Approximately 10 weeks to 2 months are needed to produce a finished 15 cm container plant from a rooted cutting.
- *Growth habit*.—Very compact, low growing and naturally freely branching.
- *Suggested container sizes*.—1 gallon-5 gallon (largest).
- *Use*.—Ornamental for use as a landscape plant or container plant.
- *Type*.—Herbaceous perennial.
- *Plant dimensions*.—After one year's growth in a 3.7 gallon container: 15 cm to 20 cm in height and 40 cm to 45 cm in width.
- *Cultural requirements*.—Grow in full sun with moderate water, and well-draining soil such as loam.
- *Hardiness*.—USDA Zone 5.
- *Growing requirements*.—If grown outside in regions which experience winter freezing, 'Orange Ruffles' may be started as a cutting during the spring or summer of the previous year, planted out prior to the onset of winter, and flowering will commence typically in March to May according to the region and season.

Stems (basal stems, flowering stems):
- *Stem shape*.—Cylindrical with slightly raised longitudinal ridges approximately 1 mm. apart.
- *Stem length*.—12 cm to 15 cm.
- *Stem diameter*.—4 mm to 5 mm.
- *Stem surface*.—Villous, hairs approximately 1 mm. apart, length 1.5 mm-2.0 mm, very fine, silver in appearance, color NN155C.
- *Stem color*.—145C, longitudinal ridges 145B.
- *Internode length*.—Ranges between 10 mm and 15 mm.
- *Branching habit*.—Basal branching.

Foliage:
- *Leaf arrangement*.—Alternate.
- *Type*.—Evergreen.
- *Leaf shape*.—Predominantly lanceolate, occasionally bearing protruding lobes conferring oak-leaf appearance.
- *Leaf apex*.—Acute.
- *Leaf base*.—Truncate.
- *Leaf margins*.—Lanceolate leaves: Irregularly slightly dentate, typically 2-3 shallow teeth per leaf edge, depth less than 0.5 mm. Leaves bearing protruding lobes: 2-4 lobes per leaf edge, lobes rounded, protruding 2 mm-7 mm.
- *Leaf surface* (*both surfaces*).—Puberulent.
- *Leaf length*.—90 mm.
- *Leaf width*.—16 mm, 22 mm at lobes where present.
- *Leaf color* (*both surfaces*).—137A.
- *Leaf attachment*.—Sessile.
- *Vein pattern*.—Pinnate, veins barely visible on either surface except midrib. Midrib raised 0.25 mm on adaxial surface and 0.5 mm. on abaxial surface.
- *Vein color* (*both surfaces*).—145C.
- *Fragrance*.—None.

Inflorescence:
- *Form*.—Solitary.
- *Aspect*.—Facing upward.
- *Dimensions of inflorescence*.—70 mm in diameter and 25 mm in height.
- *Type*.—Radiate capitate.
- *Shape*.—Radiate with center disc.
- *Flowering season*.—Spring, summer and fall.
- *Fragrance*.—Absent.
- *Self-cleaning or persistent*.—Self-cleaning.
- *Disc diameter* (*inflorescence fully expanded*).—28 mm.

*Inflorescence number per plant.*—A one-year old plant bears approximately 75 inflorescences in bud and flower at one time.

*Lastingness of inflorescence on the plant.*—10 days, reducing to 7 days in full sun in mid- summer.

Peduncle:

*Length.*—4 cm.

*Diameter.*—2.5 mm-3.0 mm.

*Shape.*—Cylindrical.

*Texture.*—Surface is lightly pubescent and exhibits faint longitudinal ridges.

*Strength.*—Stiff, wiry.

*Color.*—145C, longitudinal ridges 145B.

Flower buds (immediately prior to ray floret emergence):

*Surface.*—Villous.

*Shape, dimensions.*—Horizontal cylinder 7 mm in height, 16 mm in diameter, excluding phyllaries.

*Color.*—144B.

Ray florets (inflorescence fully expanded prior to senescence):

*Shape.*—Tubular, petals flared or fan shaped.

*Surface (both).*—Smooth, glabrous.

*Arrangement.*—Radiate.

*Number per inflorescence.*—55-65 of which 25-30 outermost ray floret are fully formed and 30-35 inner ray florets are small and irregularly malformed.

*Outer ray florets.*—Number of petals per outer ray floret: Predominantly five, very occasionally six. Fused or unfused (whether arranged tubular or in a fan): Fused, ranging between one-third of length to two-thirds of length from base. Margins: Entire. Dimensions: 35 mm in length including the corolla tube, 20 mm-30 mm in width across petal apices. Corolla tube dimensions (outer ray florets only): 12 mm in depth and 1.0 mm-1.5 mm in diameter. Color (free section, both surfaces): Open red 42C with bright yellow tips, 9C, then becoming lighter red 42D with larger yellow tips 9C. Yellow tips exhibit parallel veins color 42C. Color (fused section and base, both surfaces): Ranges between 42A and 44A.

*Inner ray florets.*—Number of petals per inner ray floret: Two petals of which one is shorter and recurved. Margins: Entire. Dimensions: Longer inner ray floret: 14 mm in length, 4 mm in width. Shorter, recurved inner ray floret: 8 mm in length, 3 mm in width. Color: (both surfaces): 42D with occasional yellow tips, 9C. Veins (inner ray florets only, both surfaces): On yellow tips only, parallel, color 42C.

Disc florets:

*Quantity per inflorescence.*—Numerous, approximately 125 to 150.

*Disc floret dimensions.*—13 mm in length and 2.5 mm in width.

*Corolla tube.*—Comprised of six longitudinally fused petals.

*Depth of disc floret corolla tube.*—4.5 mm.

*Surface of disc florets.*—Lanate.

*Color of disc florets (both surfaces).*—Corolla tube: 145C. Petals: 13B. Petal apex: 53A.

Phyllaries (involucral bracts):

*Arrangement.*—Concentric whorl consisting of larger lower and outermost bracts and smaller upper and innermost bracts which curve inwardly to clasp the bud.

*Quantity.*—Approximately 40 of which 10 large, outer and 30 small, inner.

*Shape.*—Lanceolate

*Dimensions.*—Ranging from 18 mm in length, 5.5 mm in width (larger bracts), to 9 mm in length and 2.5 mm in width (smaller bracts).

*Color (both surfaces).*—137A.

*Margin.*—Entire.

*Apex.*—Acute.

*Base.*—Truncate.

*Surface (adaxial surface).*—Smooth.

*Surface (abaxial surface).*—Pubescent, very fine silver hairs, color NN155C.

Reproductive organs (present on disc florets only):

*Stamens.*—Quantity: 5. Dimensions: 2 mm in length, less than 0.25 mm in width. Color: 17A. Form: Filamentose. Anthers: Shape: Ellipsoid. Dimensions: 1.5 mm in length and 0.25 mm in width. Color: N186C. Pollen: Plentiful, color 17A.

*Pistil.*—Style: Quantity: 1 Shape: Cylindrical. Dimensions: 5 mm in length and 0.75 mm in width. Color: 13B. Stigma: Form: Plumose. Dimensions: 1 mm in length, 0.75 mm. in width. Color: 46B. Ovary: Position: Inferior. Shape, dimensions: Globose, 1.5 mm in diameter. Color: 149C.

Fruit and seed:

*Number of seeds.*—Small to moderate amount (ranges from 50 to 100 seeds per inflorescence).

*Seed dimensions.*—5 mm 6 mm in length (including hairs at apex) and 1 mm to 2 mm in diameter.

*Seed color.*—200A.

*Seed shape.*—Conical with rounded base and apex.

*Seed surface.*—Smooth except at apex where many very fine silver hairs, up to 2 mm in length, are present in circular groups.

Disease and pest susceptibility: 'Orange Ruffles' has not been observed to exhibit any resistance to any particular pest or disease. 'Orange Ruffles' is susceptible to downy mildew and to thrips as may be typical of *Gaillardia.*

COMPARISON WITH PARENTAL LINES AND KNOWN VARIETY

'Orange Ruffles' is distinguishable from the male parent, seedling code G1409-3 as follows. Whereas the flowers of G1409-3 remain single in form and pale orange in color, the young flowers of 'Orange Ruffles' are single and red in color, becoming double, larger and orange-red in color.

'Orange Ruffles' is distinguishable from the female parent, seedling code G1317-5, as follows. Whereas the flowers of G1317-5 exhibit orange colored tubular ray florets, the ray florets of 'Orange Ruffles' are flat, single, and colored red initially becoming double and orange-red in color when fully open.

The closest comparison plant known to the inventor is *Gaillardia* 'Sunset Flash' (U.S. Plant Pat. No. 26,945). 'Sunset Flash' and 'Orange Ruffles' are similar in plant habit and in bearing orange to red flat ray florets. However, the ray florets of 'Sunset Flash' remain in single form whereas the flowers of 'Orange Ruffles' become double and orange-red in color when fully open.

I claim:

1. A new and distinct cultivar of *Gaillardia* Plant Named 'Orange Ruffles' as described and illustrated herein.

* * * * *